(12) United States Patent
Ketola et al.

(10) Patent No.: US 7,345,750 B2
(45) Date of Patent: Mar. 18, 2008

(54) METHOD OF ACCELERATED TESTING OF ILLUMINATED DEVICE COMPONENTS

(75) Inventors: Warren D. Ketola, St. Paul, MN (US); Richard M. Fischer, Jr., Hudson, WI (US)

(73) Assignee: 3M Innovative Properties Company, St. Paul, MN (US)

( * ) Notice: Subject to any disclaimer, the term of this patent is extended or adjusted under 35 U.S.C. 154(b) by 358 days.

(21) Appl. No.: 11/196,902

(22) Filed: Aug. 4, 2005

(65) Prior Publication Data

US 2006/0037413 A1    Feb. 23, 2006

Related U.S. Application Data

(63) Continuation-in-part of application No. 10/914,386, filed on Aug. 9, 2004, now Pat. No. 7,124,651.

(51) Int. Cl.
G01J 1/20    (2006.01)
G01N 17/00   (2006.01)

(52) U.S. Cl. .................. 356/229; 73/865.6

(58) Field of Classification Search .......... 73/865.6; 356/229

See application file for complete search history.

(56) References Cited

U.S. PATENT DOCUMENTS

| | | | |
|---|---|---|---|
| 3,202,811 A * | 8/1965 | Hall, Jr. ................ | 362/2 |
| 4,683,379 A | 7/1987 | Wolff | |
| 4,747,645 A * | 5/1988 | Rudzki ................. | 356/51 |
| 4,817,447 A | 4/1989 | Kashima et al. | |
| 4,931,655 A * | 6/1990 | Yoshida et al. ........ | 250/492.1 |
| 5,206,518 A * | 4/1993 | Fedor et al. ........... | 250/504 R |
| 5,220,840 A * | 6/1993 | Neigoff et al. ......... | 73/865.6 |
| 6,555,827 B1 | 4/2003 | Kockott | |
| 6,576,911 B1 | 6/2003 | Potyrailo et al. | |
| 6,604,436 B1 * | 8/2003 | Lewandowski et al. .... | 73/865.6 |
| 6,626,052 B1 | 9/2003 | Martin et al. | |
| 6,859,309 B2 * | 2/2005 | Fischer et al. ......... | 359/359 |
| 7,038,196 B2 * | 5/2006 | Scott et al. ........... | 250/252.1 |
| 2003/0133184 A1 | 7/2003 | Fischer, Jr. et al. | |
| 2004/0228141 A1 | 11/2004 | Hay et al. | |
| 2004/0233520 A1 | 11/2004 | Ketola et al. | |

FOREIGN PATENT DOCUMENTS

EP    0487202    5/1992

(Continued)

OTHER PUBLICATIONS

Pending U.S. Appl. No. 10/914,386, filed Aug. 9, 2004.

(Continued)

*Primary Examiner*—Layla G. Lauchman
*Assistant Examiner*—Jarreas Underwood
(74) *Attorney, Agent, or Firm*—Carolyn A. Fischer (57) ABSTRACT

A method of selection of an illuminator for use in an accelerated light stability test device chamber is described that employs measuring and comparing the spectral irradiance of at least one light source for use in an illuminated device and at least one illuminator suitable for use in an accelerated weathering chamber and selecting an illuminator having certain irradiance criteria. Also described are methods of accelerated light stability testing of an illuminated display components and an accelerated light stability test device.

20 Claims, 5 Drawing Sheets

FOREIGN PATENT DOCUMENTS

| | | |
|---|---|---|
| JP | 58071439 | 4/1983 |
| JP | 2002-005815 | 1/2002 |

OTHER PUBLICATIONS

Fischer, R., Ketola, W., Dittmar, R., King, R., "Analytical Studies of Spectrally Exposed Polyethylenenapthanate", Polymer Material Science and Engineering Symposium (PMSE), American Chemical Society, Washington, DC, Aug. 2000.

ASTM-D 4674-02, Standard Practice for Accelerated Testing for Color Stability of Plastics Exposed to Indoor Office Environments, 2002.

Atlas Material Testing Solutions, Laboratory Weathering Testing, 1 page from website on Jul. 28, 2004.

Atlas Material Testing Solutions, Fluorescent Devices, 1 page from website on Jul. 28, 2004.

Q-Panel Lab Products, QUV Accelerated Weathering; UVA-340, the Best Stimulation of Solar UV., 2 pages from website on Jul. 28, 2004.

Q-Panel Lab Products, QUV The World's Most Widely Used Weathering Tester, Three Models of the QUV, 1 page from website on Jul. 28, 2004.

Q-Panel Lab Products, Test Chambers, Will Your Product Last Outdoors?, 1 page from website on Jul. 28, 2004.

* cited by examiner

METHOD OF ACCELERATED TESTING OF ILLUMINATED DEVICE COMPONENTS

RELATED APPLICATIONS

This application is a continuation-in-part of U.S. patent application Ser. No. 10/914,386 filed Aug. 9, 2004 now U.S. Pat. No. 7,124,651.

BACKGROUND

Laboratory accelerated weathering test chambers and test services are described in the art. For example, three different models of accelerated weathering test devices are available from Q-panel Lab Products, Cleveland, Ohio under the trade designations "Model QUV/se", "Model QUV/spray" and "Model QUV/basic".

According to the Q-panel website (www.q-panel.com on Jul. 28, 2004), the "QUV Accelerated Weathering Tester" reproduces the damage caused by sunlight, rain, and dew. The QUV tests material by exposing them to alternating cycles of light and moisture at controlled, elevated temperatures. The QUV simulates the effect of sunlight with fluorescent ultraviolet (UV) lamps. It simulates dew and rain with condensing humidity and water sprays. Exposure conditions can be varied to simulate various end-use environments. Although UV is only about 5% of sunlight, it is responsible for most of the photochemical damage to durable materials outdoors. To simulate the damage caused by sunlight it is not necessary to produce the entire spectrum of sunlight. It is only necessary to simulate this short wave UV. The UVA-340 lamp gives an excellent simulation of sunlight in the region from 365 nm down to the solar cut-off of 295 nm. The UVA-340 produces only those UV wavelengths found in sunlight. In a few days or weeks, the QUV reproduces the damage that occurs over months or years outdoors. Types of damage include color change, gloss loss, chalking, cracking, hazing embrittlement, and strength loss. QUV test data can help in the selection of new materials, the improvements of existing material or the evaluation of changes in formulations."

Another manufacturer of commercially available laboratory weathering test chambers is Atlas Material Testing Solutions, Chicago, Ill. a supplier of xenon arc instruments, fluorescent devices, carbon arc devices and metal halide systems. According to their website (www.atlas-mts.com on Jul. 28, 2004), "Tests using fluorescent lamps are useful for relative rank comparisons between materials under specific conditions, but the comparison to service lifetime performances or correlation to outdoor exposures may not be valid."

SUMMARY

The Applicant has found that accelerated light stability test chambers using standard ultraviolet fluorescent lamps are particularly unsuitable for evaluating the performance of components used in illuminated (e.g. display) devices. Accordingly, industry would find advantage in improved methods and devices having better prediction capability. Since the accelerated light stability test chamber and the illuminated (e.g. display) device each have a light source, for the sake of clarity "light source" is used herein with reference to the illuminated (e.g. display) device and "illuminator" is used with reference to the accelerated light stability test chamber.

Unlike the known methods of accelerated light stability testing, the methods and devices described herein employ illuminators believed unknown for use as a light source in accelerated light stability test chambers.

In one embodiment, a method of accelerated light stability testing is described comprising providing one or more test specimens in a test chamber; exposing the specimen to at least light wherein an irradiance at wavelengths ranging from 300 nm to 350 nm is less than 3.1% of the irradiance at wavelengths from 300 nm and 500 nm; an irradiance at wavelengths ranging from greater than 350 nm to 380 nm ranges from 0.2% to 2.2% of the irradiance at wavelengths from 300 nm and 500 nm; an irradiance at wavelengths ranging from greater than 380 nm to 420 nm ranges from 4.5% to 9.1% of the irradiance at wavelengths from 300 nm and 500 nm; and an irradiance at wavelength ranging from greater than 420 nm to 500 nm ranges from about 86% to about 95% of the irradiance at wavelengths from 300 nm and 500 nm.

In another embodiment, an accelerated light stability test chamber is described comprising an illuminator that provides the irradiance characteristics just described.

In other embodiments, a method of accelerated light stability testing, an accelerated light stability testing chamber, and a method of selecting an illuminator for use in an accelerated light stability test chamber are described. The illuminator is selected by a) measuring the spectral irradiance for at least wavelengths ranging from 250 nm to 500 nm
   i) of at least one light source for use in an illuminated display as would be emitted during use of the light source in the illuminated display, and
   ii) of at least one illuminator suitable for use in an accelerated weathering chamber;

b) comparing the spectral irradiance measurements of the illuminator to the light source;

c) selecting an illuminator wherein
   i) a first ratio of irradiance for wavelengths below 300 nm to the irradiance at wavelengths from 300 nm to 500 nm of the illuminator ranges from about 0.2 times to 2.6 times greater than the light source or the first ratio is greater than 2.6 times greater than the light source and a filter is disposed proximate the illuminator to reduce the ratio;
   ii) a second ratio of irradiance for wavelengths from 300 nm to 400 nm to the irradiance at wavelengths greater than 400 nm to 500 nm of the illuminator ranges from about 0.9 times to about 15 times greater than the light source;
   iii) for wavelengths greater than 300 nm the illuminator has an irradiance greater than the light source, or has 50% to 100% of the irradiance of the light source and a temperature above 50° C. is employed during the accelerated light stability test.

The illuminator typically differs from the light source in size or irradiance. The spectral irradiance may be measured at increments ranging from 1 nm to 10 nm. For wavelengths greater than 300 nm the illuminator preferably has an irradiance that is greater than the light source by a factor ranging from 2 to 200. The method of selection of the illuminator may include measuring more than one light source and averaging the spectral irradiance measurements. The spectral irradiance measurements may be compared by comparing plots or by comparing the sums of the squares of the differences between the light source and at least two illuminators and selecting the illuminator with the lowest sum of squares.

The test specimen is typically a component of an illuminated (e.g. display) device such as a liquid crystal display device. The display device may include a mobile telephone, hand-held computer device, personal data assistant, electronic game, computer monitor, and a television screen. The component may include an optical film such as a prism film, a polarizing film, a diffusive film, and combinations thereof. The component may also be reflective polarizer, an absorptive polarizer, a light guide, a diffusive component, a transparent plate, as well as an adhesive composition. The light source of such displays is typically a cold cathode fluorescent light source or a mercury lamp having filters.

During testing of the test specimen, the exposure may ranges from 24 hours to 5000 hours. In some embodiments, the test chamber is maintained at a temperature ranging from 40° C. to 100° C. During testing, the humidity may range from 1 time to 30 times of the absolute humidity of the display component during use. The illuminator may comprise a xenon-arc lamp, a metal halide lamp, or a fluorescent lamp.

DETAILED DESCRIPTION

Various display devices include a viewing surface and a (e.g. underlying) light source. For example, liquid crystal displays share the common feature of having a liquid crystal display illuminated by a light source. Such liquid crystal displays (LCDs) are commonly employed in illuminated display articles including mobile telephones, hand-held computer devices such as personal data assistants (PDAs) and electronic games, as well as laptop computers, LCD monitors and television screens. Various other optical components, such as optical films, are often positioned between the liquid crystal display and the light source.

To increase consumer confidence in the purchase of an illuminated display device, the manufacturer of the display device often warrantees the device for a specified duration of time. Accordingly, it is desirable to accurately predict the service life of the display device. This can be accomplished to at least some extent by evaluation of the various individual components and materials intended for use in the illuminated display.

The Applicant has found that the test results obtained from standard accelerated weathering test chambers employing lamps (i.e. illuminators) intended for use in such accelerated weathering test chambers have poor correlation to actual service life when used to evaluate illuminated display components. It is surmised that the lack of correlation between the accelerated weathering test results and actual service life is attributed to the illuminator of the accelerated weathering device. In the case of illuminated display devices as well as other devices having an integral or non-integral artificial light source, sunlight is not the major source of light exposure, and thus not the major cause of photochemical damage. Rather, the illuminator of the illuminated (e.g. display) device is the major source of light exposure.

In order to simulate the effects of the light present in an illuminated display device, the Applicant has characterized the spectral emission of a light source of an illuminated display device of interest as would be emitted during use of the light source in the illuminated display. For example, if the light source includes an optical filter, the spectral emission of the light source with the filter is characterized. A suitable illuminator was then selected having a sufficient spectral match to the actual light source of the illuminated display. The illuminator for use in the accelerated light stability test chamber typically differs from the light source of the illuminated display device in either its physical size and/or its irradiance. Many light sources employed in display devices are unable to generate high intensities of light to accelerate testing without breaking or creating excessive amounts of heat. The selected illuminator can then be employed in an accelerated weathering test chamber. Accordingly, the method and accelerated weathering device described herein may employ commercially available accelerated weathering test chambers, such as those previously described, modified by the selection of an illuminator having certain spectral properties.

Various known instruments are suitable for characterizing the spectral emission of a light source and illuminator. One illustrative instrument is a spectroradiometer commercially available from Optronic Laboratories, Inc. Orlando, Fla. under the trade designation "Optronics OL754" calibrated with a standard source of irradiance traceable to the National Institute for Standards and Technology, Gaithersberg, Md.

The spectral irradiance of the light source of the illuminated (e.g. display) device as well as candidate illuminators of interest for use in an accelerated light stability test chamber are characterized by measuring the spectral irradiance. The spectral irradiance is typically measured at least at wavelengths ranging from about 250 nm to about 500 nm. The spectral irradiance may be measured at wavelength increments ranging from about 1 nm increments to about 10 nm increments. The spectral irradiance may be measured at any increment between 1 nm and 10 nm, with increments of 1 nm to 2 nm being preferred.

After measuring the spectral irradiance of the light source of the illuminated (e.g. display) device and one or more illuminators being considered for use in the accelerated light stability test chamber, the spectral irradiance measurements are compared for example by comparing plots. Alternatively, the measurements may be compared by comparing the sums of the squares of the differences between the light source and at least two illuminators and selecting the illuminator with the lowest sum of squares. The sum of squares=$\Sigma (I_{acc}-I_{dis})^2$ where $I_{acc}$ is the irradiance of the illuminator in the accelerated test device and $I_{dis}$ is the irradiance of the light source in the display (watts/m$^2$ per nm), and is summed from 300 nm to 500 nm at each measured wavelength (e.g. at 2 nm increments).

The method of selection of the illuminator may also include measuring more than one light source and averaging the spectral irradiance measurements. Further, a combination of two or more illuminators may be employed to provide the desired irradiance. If more than one illuminator is employed, the test chamber may include a rotating specimen drum or the test specimens may be manually repositioned at regular intervals to provide the same net exposure to each specimen.

The total irradiance of the wavelength range is typically not a good indicator since the total irradiance alone does not take into account the distribution of the irradiance. Accordingly, the total spectral irradiance can be divided into at least two and as many as ten or more fractions. In at least some embodiments, it has been found useful to divide the total irradiance into four fractions. Specific fractions of interest include 1) irradiance for wavelengths ranging from about 300 nm to about 350 nm, 2) irradiance for wavelengths greater than 350 nm to about 380 nm, 3) irradiance for wavelengths greater than 380 nm to about 420 nm, and 4) irradiance for wavelengths greater than 420 nm to about 500 nm. An illuminator for use in an accelerated weathering test chamber is chosen wherein each fraction has sufficient spectral match to that of the light source of the illuminated (e.g. display) device of interest.

In embodiments of the invention, the irradiance at wavelengths from about 300 nm to about 500 nm can be of greatest interest. For example, increasing yellowness of certain plastic materials such as polyethylene naphthalate (PEN) is typically caused by wavelengths ranging from about 300 nm to about 400 nm; whereas loss of yellowness (e.g. "photobleaching") is typically caused by wavelengths ranging from about 400 nm to 500 nm. In view of these effects, it is preferred that the ratio of irradiance for wavelengths from 300 nm to 400 nm to the irradiance at wavelengths greater than 400 nm to 500 nm of the illuminator ranges from about 0.9 times to about 15 times greater than the light source. In doing so, the accelerated light stability test is designed to produce the same yellowing effect as the light source of the illuminated device or error on the side of increasing, rather than decreasing yellowness.

Light sources for illuminated display devices typically do not have significant irradiance at wavelengths below 300 nm. The ratio of irradiance for wavelengths below 300 nm to the irradiance at wavelengths from 300 nm to 500 nm of the illuminator typically ranges from about 0.2 times to 2.6 times greater than the light source. Alternatively, the illuminator may have an irradiance greater than 2.6 times the light source and a (e.g. UV cut-on) filter is disposed proximate the illuminator to reduce the specified ratio.

In embodiments of the invention, the illuminator for use in the accelerated light stability test preferably provides an irradiance greater than the light source, particularly for wavelengths greater than 300 nm. In some embodiments, the illuminator may have any irradiance that is greater than the light source of the illuminated (e.g. display) device by a factor ranging from about 2 to about 200. This level of irradiance intensity can advantageously used to accelerate the exposure without increasing the temperature above 50° C. Alternatively, the illuminator may have an irradiance that ranges from about 50% to 100% of the irradiance of the light source. However, in such embodiments, temperatures ranging from about 50° C. to about 100° C. are typically employed to accelerate the test. Temperatures can range from about 50° C. to about 100° C. for illuminators having an irradiance greater than the light source. However, such higher temperatures are not required.

Wavelengths of greater than 500 nm typically do not contribute to chemical degradation. If however the light source emits significant intensity of light at wavelengths greater than 500 nm, the spectral irradiance of the light source and the illuminator may be characterized at wavelengths up to about 800 nm, or up to about 1600 nm. A suitable illuminator for use in an embodied accelerated weathering device provides at least light wherein 1) the irradiance at wavelengths ranging from 300 nm to 350 nm is less than 3.1% of the irradiance at wavelengths from 300 nm and 500 nm; 2) the irradiance at wavelengths ranging from greater than 350 nm to 380 nm ranges from 0.2% to 2.2% of the irradiance at wavelengths from 300 nm and 500 nm; 3) the irradiance at wavelengths ranging from greater than 380 nm to 420 nm ranges from 4.5% to 9.1% of the irradiance at wavelengths from 300 nm and 500 nm; and 4) the irradiance at wavelengths ranging from greater than 420 nm to 500 nm ranges from about 86% to about 95% of the irradiance at wavelengths from 300 nm and 500 nm. The rectangular integration is conducted so there is no overlap of the individual bandpasses.

Employing an illuminator having the spectral distribution properties just described has been found to be of particular utility for evaluating (e.g. cold cathode fluorescent) LCD television components (e.g. laminated optical films and the adhesive thereof). An illustrative commercially available lamp having such spectral characteristics is commercially available from Philips Lighting Co., Somerset, N.J. under the trade designation "Phillips F40 50U".

The method of determining (e.g. measuring) the spectral irradiance of the light source of at least one illuminated (e.g. display) device, optionally averaging the spectral irradiance measurements for repeat measurements of each of the light sources, and selecting a lamp suitable for use in an accelerated weathering test chamber having similar spectral distribution properties to that of the illuminated (e.g. display) device can be employed to select an illuminator suitable for accelerated weathering testing in order to approximate the service life of an illuminated (e.g. display) device component. It is appreciated, however, that the target fractional irradiance values as well as the wavelength range of the fractions vary depending on the light source of the illuminated (e.g. display) device of interest.

Figure 5:
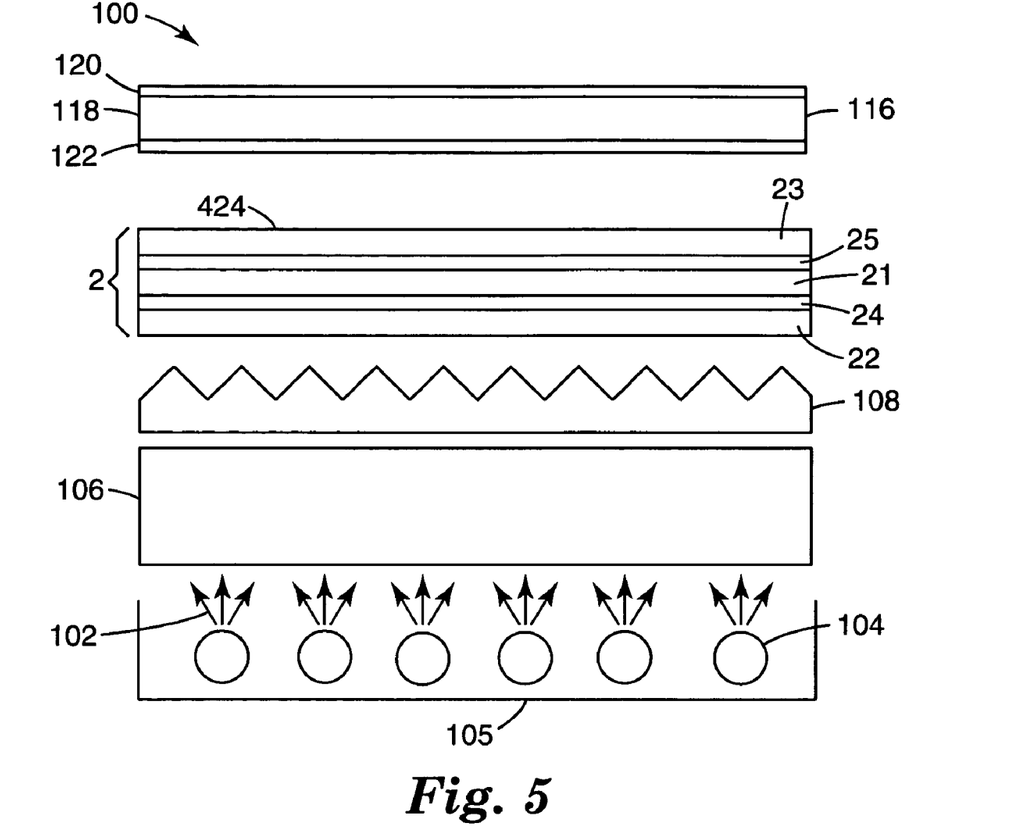
FIG. 5 is a schematic view of an illustrative liquid crystal display ("LCD") television display.

The method and device embodied herein are useful for predicting (e.g. relative) durability of components of liquid crystal display televisions. As illustrated by FIG. 5 as follows, illuminated displays typically include an assembly of several individual components including optical films (e.g. prism films, polarizing films, diffusive films, and combinations thereof) as well as components that are not necessarily films such as reflective polarizers, absorptive polarizers, light guides, diffusive components, transparent plates; as well as various adhesive compositions that may be employed.

An illustrative display for LCD television screens and other large displays is schematically illustrated in FIG. 5. In the display 100 illustrated in FIG. 5, light 102 is generated by one or more light sources 104. The light sources 104 may be any suitable type of light source, or combination of light sources, that achieves the desired color in the illuminating light 102. Examples of light sources include cold cathode fluorescent tubes, light emitting diodes and the like. A reflector 105 may be positioned behind the light sources 104 to reflect light that is emitted away from the display back towards the display. The reflector 105 may be a diffuse reflector so as to help make the illumination of the display more uniform. The reflector 105 may take one of several different forms, including that of a sheet reflector placed below the light sources 104 and also that of a reflecting box or cavity (illustrated) with reflecting surfaces along the side. The reflector 105 need not be flat, and may have a desired shape.

The light 102 enters a diffusing plate 106, which is used to diffuse the light so that the viewer perceives uniform image brightness across the display 100. The diffusing plate 106 may be a few millimeters thick to provide rigidity, and may contain diffusing particles. The diffusing plate 106 may be formed of any suitable material, for example polycarbonate or poly methyl methacrylate (PMMA).

After passing through the diffusing plate 106, the light has a wide viewing angle. Television screens typically use a wide horizontal viewing angle so that viewers may be able to see the image from a wide range of angles relative to the screen normal. The vertical viewing angle, on the other hand is typically less than the horizontal viewing angle, since the vertical position of the viewers relative to the screen normal is usually spread over a much smaller range than the horizontal spread. Therefore, it is advantageous to reduce the vertical viewing angle relative to the horizontal viewing angle, which results in the image becoming brighter. A layer of prismatic brightness enhancing film 108 may be used to reduce the vertical viewing angle of the light that has passed through the diffusing plate 106. An air gap may be present between the film 108 and the diffusion plate 106, or there may be intervening layers between the film 108 and the plate 106.

The LCD 116 usually includes a layer of liquid crystal 118 sandwiched between first and second absorbing polarizers 120 and 122, respectively. The light 102 from the light sources 104 is typically unpolarized, so a laminated optical article 2 comprising a reflective polarizer 21 adhesively bonded with adhesive layers 25 and 24 between two diffusive films 22 and 23, may be inserted between the brightness enhancing layer 108 and the LCD 116 to recycle the light in the polarization state that would otherwise be absorbed in the second absorbing polarizer 122. The light reflected by the reflective polarizer 21 may subsequently have its polarization rotated, at least partially, for example through diffuse reflection or by passing through a polarization rotating element (not shown). When it is returned to the reflective polarizer 21, at least a portion of the reflected light is in the polarization state that is transmitted reflecting polarizer 22 and the second absorbing polarizer 122.

Light that has passed through the laminated optical article 2 is then directed to the LCD 116, which imposes an image on the light passing to the viewer. The second absorbing polarizer 122 may remain separated from the laminated optical article 2, or may be adhered with the adhesive. The outer surface 124 of the first absorbing polarizer 120 may be treated with one or more surface treatments. For example, the outer surface 124 may be provided with a matte finish or an anti-glare coating. The outer surface 424 may also be provided with a hard coating to provide protection against scratching.

Additional diffusion may be provided within the screen 100, in addition to that provided in the diffusion plate 106, such as by the diffusive films layers 22 and 23 of the laminated optical article.

Additional layers and/or surface treatments may be used. For example, the upper surface of the laminated optical article may be a matte surface so as to increase light diffusion and thus increase the uniformity of the illumination of the light. One or more layers of the displays may be provided with an antistatic coating, for example a thin layer of electrically conductive material. One example of a suitable conductive material is indium tin oxide (ITO), although other conductive materials, such as conducting polymers, may be used.

Advantages of the invention are further illustrated by the following examples, but the particular lamps and exposure conditions thereof recited in the examples, as well as other conditions and details, should not be construed to unduly limit the invention.

EXAMPLES

Test Methods

Spectral irradiance measurements were conducted with a spectroradiometer, commercially available from Optronic Laboratories, Inc. Orlando, Fla. under the trade designation "Optronics OL754" that was calibrated with a standard source of irradiance traceable to National Institute for Standards and Technology, Gaithersberg, Md. For the spectral irradiance measurements of the back light units of the LCD televisions, the entrance port of the integrating sphere of the spectroradiometer was positioned as close as possible to the plane in which the optical sheet components would be positioned in actual use. For the spectral irradiance measurements of the single cold cathode lamps, the lamp was placed directly in front of the entrance port of the integrating sphere of the OL754 spectroradiometer.

Spectral irradiance measurements were conducted to characterize the emission of the cold cathode fluorescent (CCF) lamps used in the back light units of three different LCD televisions (Samsung 42"—Samsung Electronics America, Ridgefield Park, N.J., Sharp 30" Sharp Electronics Corporation, Mahwah, N.J., and LG-Phillips 32", LG Phillips LCD Company, Ltd, Seoul, Korea), a single cold cathode fluorescent lamp (Sanken Electric Company, Ltd, Japan), and a single cold cathode fluorescent lamp taken from a 15" LCD monitor (LG Phillips LCD Company).

Figure 1:
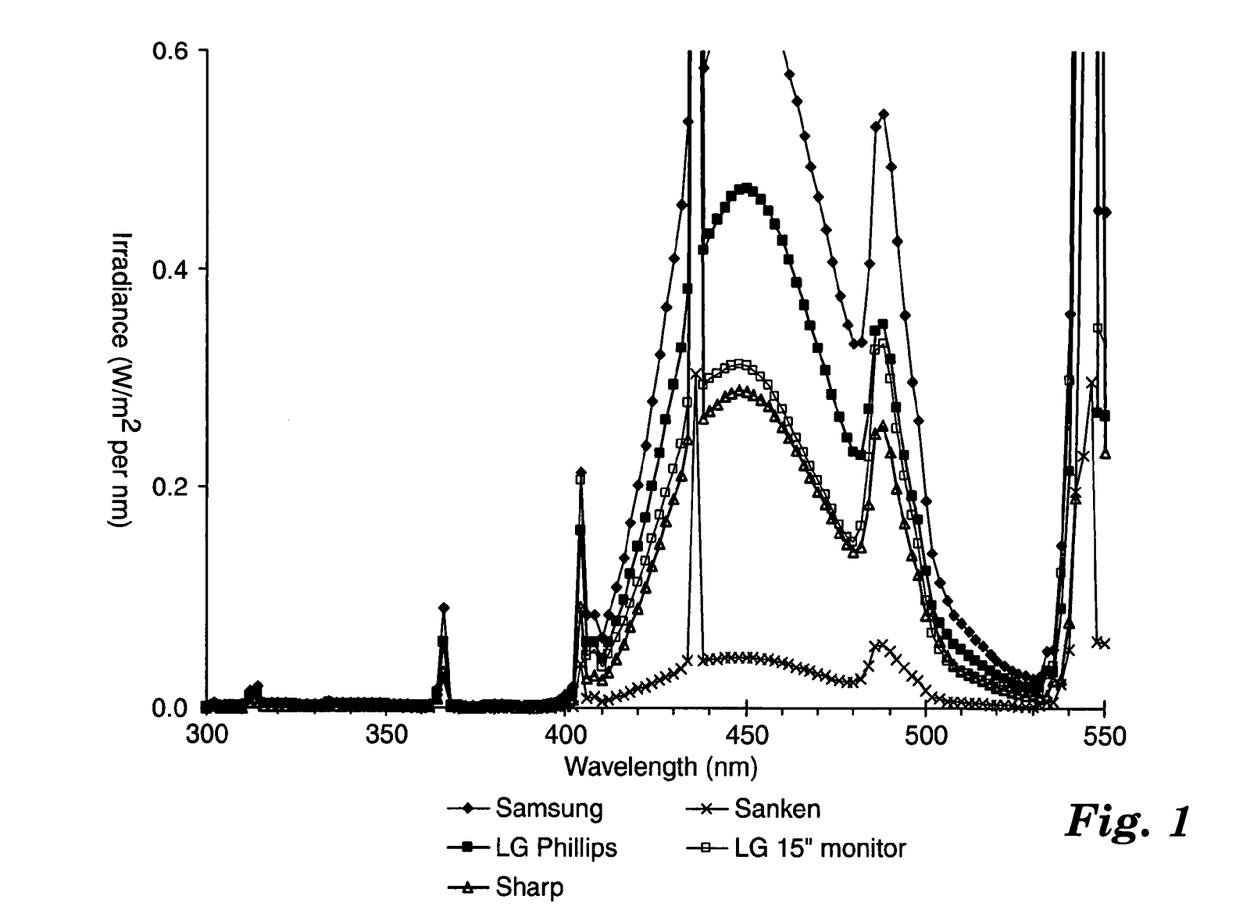
FIG. 1 is a spectral irradiance plot of the light emitted by the cold cathode fluorescent light sources of commercially available LCD displays.
Figure 2:
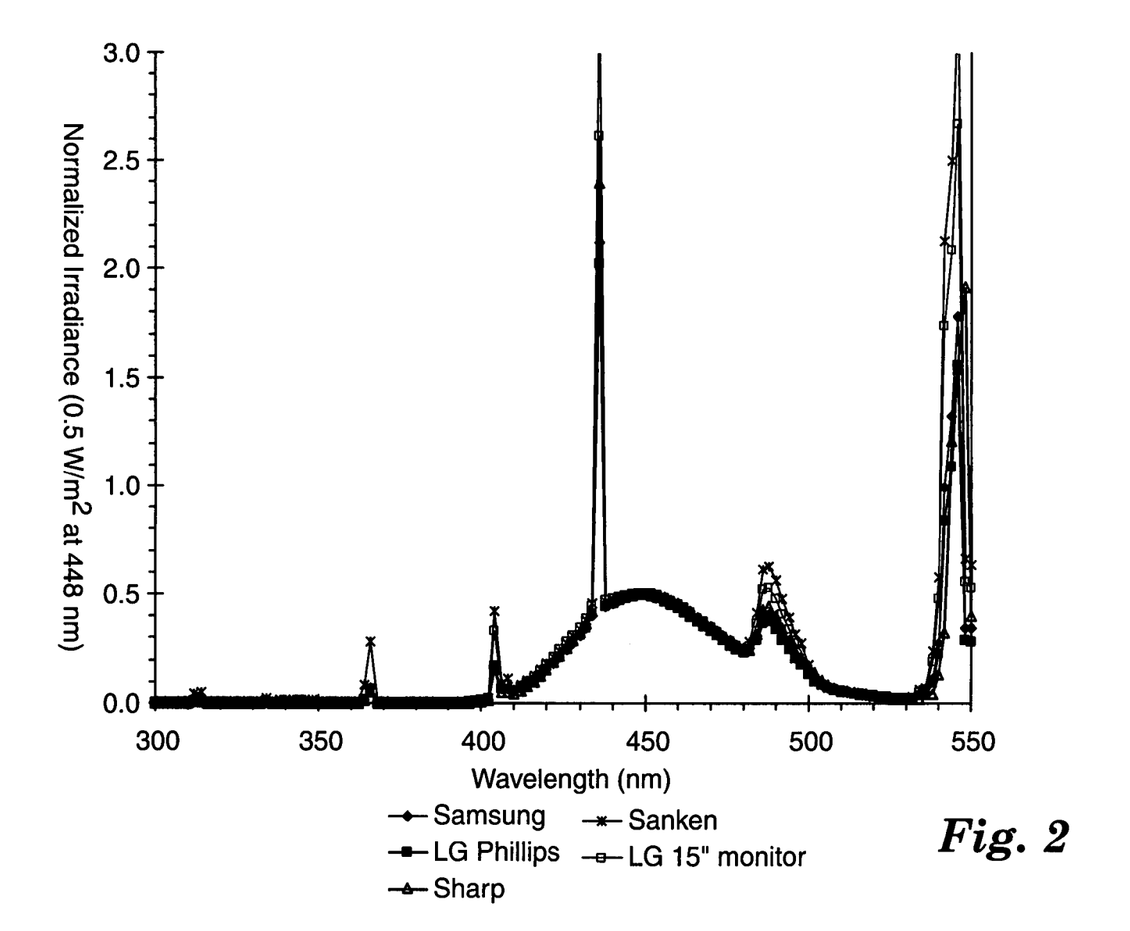
FIG. 2 is a normalized spectral irradiance plot of the light emitted by the cold cathode fluorescent light sources of commercially available LCD displays.

FIG. 1 is a spectral irradiance plot of the output for the back light units for three different LCD televisions as well as the single cold cathode lamp. FIG. 2 is the same data normalized to 0.5 W/m$^2$ at 448 nm. FIG. 2 shows that the spectral irradiance in the region of phosphor emission for cold cathode fluorescent lamps used in all the devices is the same.

Figure 3:
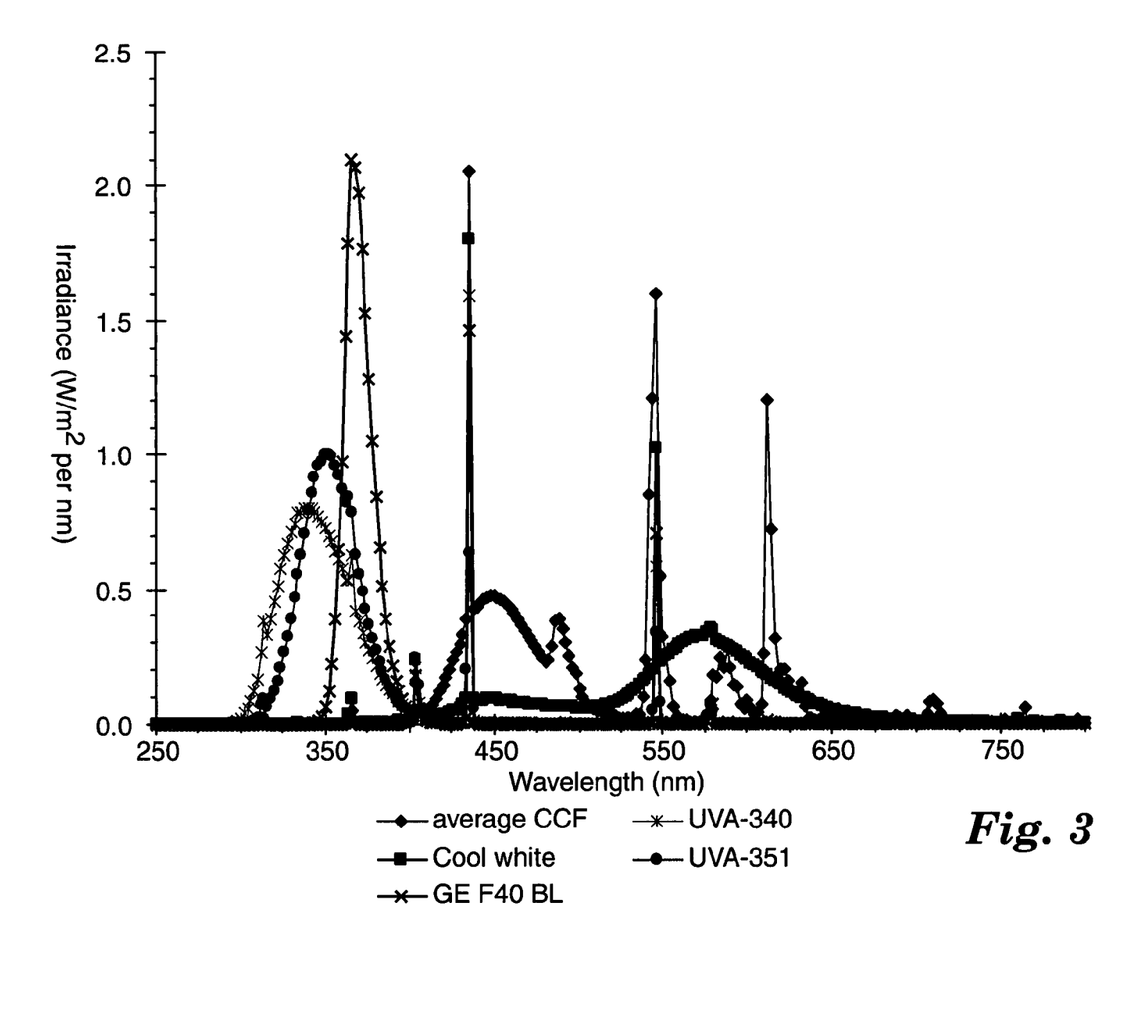
FIG. 3 is the spectral irradiance plot for fluorescent lamps used in typical accelerated light stability exposure tests in comparison to the average spectral irradiance for the cold cathode fluorescent lamps used in commercially available LCD displays.

FIG. 3 is a plot of the spectral irradiance of several fluorescent lamps compared to the average spectral irradiance for cold cathode fluorescent lamps. Fluorescent UVA-340 and UVA-351 lamps are described in ASTM G 154. The UVA-340 lamp has a peak emission at 343 nm and the UVA-351 lamp has a peak emission at 350 nm. The fluorescent black light has a peak emission near 365 nm. ASTM D 4674 describes use of cool white fluorescent lamps for exposure tests. The cool white lamps have a peak emission at 578-580 nm.

The spectral irradiance data for the average cold cathode fluorescent (CCF) lamp shown in FIG. 3 is the average for the cold cathode fluorescent lamps measured in the three LCD televisions backlight units. The spectral irradiance data for the other lamps in FIG. 3 was obtained by placing the entrance port of the integrating sphere of the OL754 spectroradiometer at the specimen plane of a accelerated light stability test chamber commercially available from Q-Panel Company, Cleveland, Ohio under the trade designation "QUV/basic fluorescent UV exposure device" operating while the irradiance was measured.

FIG. 3 shows that the spectral irradiance characteristics of the fluorescent lamps used in typical exposure tests are a poor match to the spectral irradiance for the average cold cathode lamps used as back lights in electronic devices with liquid crystal displays. Some lamps (UVA-340, UVA-351, and F40-BL) have very high levels of UV radiation. Others (the GE and Sylvania cool white lamps) are weak in the area of primary emission of the cold cathode fluorescent lamps.

Figure 4:
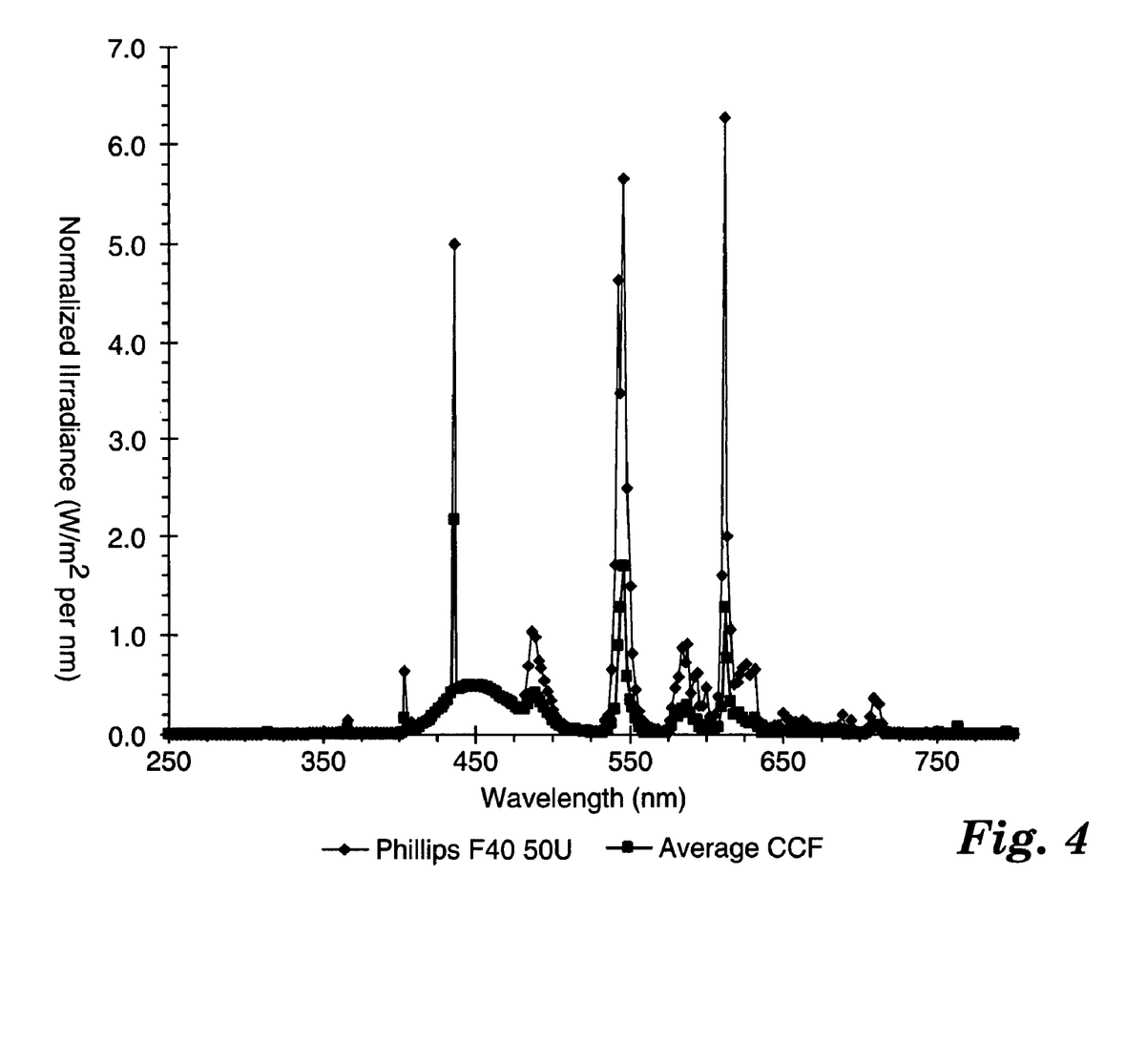
FIG. 4 is the normalized spectral irradiance of a lamp suitable for use in an accelerated weathering test chamber in comparison to the average spectral emission of the cold cathode fluorescent backlight units of FIG. 1.

FIG. 4 is a normalized spectral irradiance plot comparing the average cold cathode fluorescent lamps used as backlights in electronic devices in comparison to a Phillips F40 50U fluorescent lamp. The spectral irradiance of the Phillips F40 50U fluorescent lamp was determined by placing the entrance port of the integrating sphere of the Optronics OL754 spectroradiometer at the specimen plane of a QUV™ brand fluorescent UV device operating with the Phillips F40 50U lamps. The spectral irradiance of the Phillips F40 50U fluorescent lamp is a close match to that of the cold cathode fluorescent lamps, especially in the area of peak phosphor emission at 448 nm. A total of seventeen fluorescent lamps were tested, but the Phillips F40 50U lamp, the Sylvania D800 6500K lamp (OSRAM Sylvania, Danvers, Mass.), and the Phillips F32T8/TL850 lamp provided the closest spectral match.

The Phillips F40 50U was employed in an accelerated weathering test device obtained from Q-panel Lab Products, Cleveland, Ohio under the trade designations "Model QUV/ basic".

This accelerated weathering test device was used to evaluate a laminated optical article having a polarizing layer adhesively bonded between first and second diffusive optical films as described in further detail in U.S. patent application Ser. No. 10/914,555, filed Aug. 9, 2004; incorporated herein by reference. The yellowness color of laminated optical article in the 1976 CIE L* a* b* color space, (Delta b*(t-0), was measured using a BYK Gardner Colorsphere having a 400 nm to 700 nm spectra exposure. The laminated optical articles test specimens were subjected to accelerated aging by exposing the specimens to spectral irradiance for 300 hours at a panel temperature of 90° C. The change in yellowness (i.e. change in delta b*) is the difference between the yellowness before exposure in comparison to after exposure.

The adhesive composition of the Comparative Examples A and B was found to yellow. This result correlated with actual use data that had been reported. When tested under the same condition with the "GE F40 BL" lamp, the diffusive film was found to yellow rather than the adhesive. This result was not consistent with actual use data that had been reported.

What is claimed is:

1. A method of accelerated light stability testing comprising exposing at least one component of an illuminated display having a light source in an accelerated light stability test device wherein the test device has an illuminator selected by
a) measuring the spectral irradiance for at least wavelengths ranging from 250 nm to 500 nm
   i) of at least one light source for use in an illuminated display as would be emitted during use of the light source in the illuminated display, and
   ii) at least one illuminator suitable for use in an accelerated weathering chamber;
b) comparing the spectral irradiance measurements of the illuminator to the light source;
c) selecting an illuminator wherein
   i) a first ratio of irradiance for wavelengths below 300 nm to the irradiance at wavelengths from 300 nm to 500 nm of the illuminator ranges from about 0.2 times to 2.6 times greater than the light source or the first ratio is greater than 2.6 and a filter is disposed proximate the illuminator to reduce the first ratio;
   ii) a second ratio of irradiance for wavelengths from 300 nm to 400 nm to the irradiance at wavelengths greater than 400 nm to 500 nm of the illuminator ranges from 0.9 times to about 15 times greater than the light source;
   iii) for wavelengths greater than 300 nm the illuminator has an irradiance greater than the light source, or has 50% to 100% of the irradiance of the light source and temperatures above 50° C. are employed during the accelerated light stability test.

2. The method of claim 1 wherein the illuminator differs from the light source in size or irradiance.

3. The method of claim 1 wherein measuring the spectral irradiance is accomplished at increments ranging from 1 nm to 10 nm.

4. The method of claim 1 wherein for wavelengths greater than 300 nm the illuminator has an irradiance that is greater than the light source by a factor ranging from 2 to 200.

5. The method of claim 1 further comprising measuring more than one light source and averaging the spectral irradiance measurements.

6. The method of claim 1 wherein the spectral irradiance measurements are compared by comparing plots.

7. The method of claim 1 wherein the spectral irradiance measurements are compared by comparing the sums of the squares of the differences between the light source and at least two illuminators and selecting the illuminator with the lowest sum of squares.

8. The method of claim 1 wherein the test comprises exposure to humidity ranging from 1 time to 30 times of the absolute humidity of the display component during use.

9. The method of claim 1 wherein the illuminator is selected from a xenon-arc lamp, a metal halide lamp, or a fluorescent lamp.

10. The method of claim 1 wherein the light source is a cold cathode fluorescent light source or a mercury lamp having filters.

11. The method of claim 1 wherein the exposure ranges from 24 hours to 5000 hours.

12. The method of claim 1 wherein the test chamber is maintained at a temperature ranging from 40° C. to 100° C.

13. The method of claim 1 wherein the illuminated display device is a liquid crystal display device.

14. The method of claim 13 wherein the display device is selected from the group comprising a mobile telephone, hand-held computer device, personal data assistant, electronic game, computer monitor, and a television screen.

15. The method of claim 1 wherein the component is an optical film.

16. The method of claim 15 wherein the optical film is selected form the group comprising a prism film, a polarizing film, a diffusive film, and combinations thereof.

17. The method of claim 1 wherein the component is selected from the group comprising a reflective polarizer, an absorptive polarizer, a light guide, a diffusive component, and a transparent plate.

18. The method of claim 1 wherein the component is an adhesive composition.

19. A method of selection of an illuminator for use in an accelerated light stability test device chamber comprising:
a) measuring the spectral irradiance for at least wavelengths ranging from 250 nm to 500 nm i) of at least one light source for use in an illuminated device as would be emitted during use of the light source in the illuminated device, and ii) of at least one illuminator suitable for use in an accelerated weathering chamber;

b) comparing the spectral irradiance measurements of the illuminator to the light source;

c) selecting an illuminator wherein i) a first ratio of irradiance for wavelengths below 300 nm to the irradiance at wavelengths from 300 nm to 500 nm of the illuminator ranges from about 0.2 times to 2.6 times greater than the light source or the first ratio is greater than 2.6 and a filter is disposed proximate the illuminator to reduce the first ratio;

ii) a second ratio of irradiance for wavelengths from 300 nm to 400 nm to the irradiance at wavelengths greater than 400 nm to 500 nm of the illuminator ranges from about 0.9 times to about 15 times greater than the light source;

iii) for wavelengths greater than 300 nm the illuminator has an irradiance greater than the light source, or has 50% to 100% of the irradiance of the light source and temperatures above 50° C. are employed during the accelerated light stability test.

20. An accelerated light stability test device comprising:

a chamber; and an illuminator selected according to claim 19.

* * * * *